(12) United States Patent
Eichenbaum et al.

(10) Patent No.: US 11,273,203 B2
(45) Date of Patent: Mar. 15, 2022

(54) METHODS OF MITIGATING TOXIC EFFECTS OF VESICANTS AND CAUSTIC GAS

(71) Applicants: Janssen Pharmaceutica NV, Beerse (BE); Rutgers, The State University of New Jersey, New Brunswick, NJ (US)

(72) Inventors: Gary Eichenbaum, Belle Mead, NJ (US); Edward John Yurkow, Hillsborough, NJ (US)

(73) Assignees: Janssen Pharmaceutica NV, Beerse (BE); Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/751,961

(22) Filed: Jan. 24, 2020

(65) Prior Publication Data

US 2020/0237870 A1   Jul. 30, 2020

Related U.S. Application Data

(60) Provisional application No. 62/796,754, filed on Jan. 25, 2019.

(51) Int. Cl.
*A61K 38/19* (2006.01)
*A61P 39/02* (2006.01)
*A61K 45/06* (2006.01)
*A61K 9/00* (2006.01)

(52) U.S. Cl.
CPC .......... *A61K 38/196* (2013.01); *A61K 9/0019* (2013.01); *A61K 45/06* (2013.01); *A61P 39/02* (2018.01)

(58) Field of Classification Search
CPC .................................................. A61K 38/196
See application file for complete search history.

(56) References Cited

U.S. PATENT DOCUMENTS

| 5,869,451 A | 2/1999 | Dower |
| 6,660,843 B1 | 12/2003 | Feige |
| 7,091,311 B2 | 8/2006 | Dower |
| 7,576,056 B2 | 8/2009 | MacDonald |
| 7,615,533 B2 | 11/2009 | Yurkow |
| 8,227,422 B2 | 7/2012 | Dower |

(Continued)

FOREIGN PATENT DOCUMENTS

| WO | 199325221 | 12/1993 |
| WO | 199417784 | 10/1994 |

(Continued)

OTHER PUBLICATIONS

Glossary of Terms Agency for Toxic Substances and Disease Registry (ATSDR) [online] [2017 archived version accessed Dec. 7, 2020 from https://web.archive.org/web/20171019112231/https://www.atsdr.cdc.gov/glossary.html] (Year: 2017).*

(Continued)

*Primary Examiner* — Prema M Mertz
(74) *Attorney, Agent, or Firm* — Ice Miller LLP

(57) ABSTRACT

Methods and kits for mitigating a toxic effect of at least one of vesicants and caustic gases in a subject in need thereof are described. In particular, an effective amount of a thrombopoietin (TPO) mimetic, such as RWJ-800088 or romiplostim, is used to mitigate the toxic effect of the vesicant or caustic gas.

18 Claims, 7 Drawing Sheets

Specification includes a Sequence Listing.

(56) References Cited

U.S. PATENT DOCUMENTS

| | | |
|---|---|---|
| 2003/0083321 A1 | 5/2003 | Lerner |
| 2003/0158116 A1 | 8/2003 | Dower |
| 2005/0137133 A1 | 6/2005 | MacDonald |
| 2006/0040866 A1 | 2/2006 | MacDonald |
| 2006/0210542 A1 | 9/2006 | Yurkow |
| 2007/0148091 A1 | 6/2007 | Dower |
| 2008/0119384 A1 | 5/2008 | Yurkow |
| 2012/0070434 A1* | 3/2012 | Springhorn ............... A61P 7/04 424/134.1 |
| 2014/0047572 A1* | 2/2014 | Chen ...................... A61K 45/06 800/18 |

FOREIGN PATENT DOCUMENTS

| | | |
|---|---|---|
| WO | 2007021572 | 2/2007 |
| WO | 2007094781 | 8/2007 |
| WO | 2008086025 | 7/2008 |
| WO | 2009148954 | 12/2009 |
| WO | 2014028509 | 2/2014 |

OTHER PUBLICATIONS

Hocken and Bradshaw. "Arsine poisoning". Brit. J. industr. Med., 1970, 27, 56-60. (Year: 1970).*

Watson and Griffin. "Toxicity of Vesicant Agents Scheduled for Destruction by the Chemical Stockpile Disposal Program". Environmental Health Perspectives vol. 98, pp. 259-280, 1992. (Year: 1992).*

Liem-Moolenaar et al. "Pharmacodynamics and Pharmacokinetics of the Novel Thrombopoietin Mimetic Peptide RWJ-800088 in Humans". Clin Pharmacol Ther. Oct. 2008; 84(4):481-7 (Year: 2008).*

Wilkinson et al. "Arsine Toxicity Aboard the Asiafreighter". British Medical Journal, 1975, 3, 559-563. (Year: 1975).*

"Highlights of Prescribing Information". FDA. Rev. Dec. 2011. [online][accessed from www.accessdata.fda.gov/drugsatfda_docs/label/2011/125268s077lbl.pdf] (Year: 2011).*

Fenaux et al. "Romiplostim monotherapy in thrombocytopenic patients with myelodysplastic syndromes: long-term safety and efficacy". British Journal of Haematology, 2017, 178, 906-913. (Year: 2017).*

Berthelot-Richer et al. "Romiplostim efficacy in an acute myeloid leukemia patient with transfusion refractory thrombocytopenia", Transfusion. Apr. 2012;52(4):739-41 (Year: 2012).*

Ener et al. "Extravasation of systemic hemato-oncological therapies", Annals of Oncology 15: 858-862, 2004 (Year: 2004).*

Mayo Clinic Staff. "Petechiae" [online][2014 archived version accessed on May 26, 2021 from web.archive.org/web/20140302024131/https://www.mayoclinic.org/symptoms/petechiae/basics/causes/sym-20050724] (Year: 2014).*

Schipperus et al. "Assessment of Self-Administration of Romiplostim after Receipt of Home Administration Training Materials: A Cross-Sectional Study of Patients with Immune Thrombocytopenic Purpura and Caregivers". Blood (2016) 128 (22): 4918 (Year: 2016).*

Al-Samkari et al. in "The use of romiplostim in treating chemotherapy-induced thrombocytopenia in patients with solid tumors", haematologica 2018; 103:e170. (Year: 2018).*

Burris et al. "Pegfilgrastim on the Same Day Versus Next Day of Chemotherapy in Patients With Breast Cancer, Non-Small-Cell Lung Cancer, Ovarian Cancer, and Non-Hodgkin's Lymphoma: Results of Four Multicenter, Double-Blind, Randomized Phase II Studies"; J Oncol Pract. May 2010;6(3):133-40 (Year: 2010).*

CCO Formulary. "mitoXANTHRONE" (Aug. 2016; online version accessed on May 26, 2021 from cancercareontario.ca/sites/ccocancercare/files/mitoxantrone.pdf; newly cited, hereafter CCO Formulary) (Year: 2016).*

Hande et al in "Pharmacokinetics of High-Dose Etoposide (VP-16-213) Administered to Cancer Patients" Cancer Research 44, 379-382, Jan. 1984 (Year: 1984).*

Baker et al., Cardiovasc. Res. 77(1):44-53 (2008).
Chan et al., Eur. J. Heart Fail. 13(4):366-76 (2011).
Erickson-Miller CL, et al. "Discovery and characterization of a selective, non-peptidyl thrombopoietin receptor agonist," Exp. Hematol., 2005;33:85-93.
Ku et al., Blood, 87:4544-4551 (1996).
Langer et al., J. Mol. Cell Cardiol. 47(2):315-25 (2009).
Li et al., Blood 98(12):3241-8 (2001).
Mitchell and Bussell, Semin. Hematol. 52(1):46-52 (2015).
Nakamura T, et al. "A novel non-peptidyl human c-Mpl activator stimulates human megakaryopoiesis and thrombopoiesis," Blood. 2006;107:4300-7.
Sitnicka et al., Blood, 87:4998-5005 (1996).
Zhou et al., J. Cereb Blood Flow Metab. 31(3):924-33 (2011).
Cines et al., "Integrated analysis of long-term safety in patients with chronic immune thrombocytopaenia (ITP) treated with the thrombopoietin (TPO) receptor agonist romiplostim", International Journal of Hematology, Elsevier Science Publishers, NL, vol. 102, No. 3, Jul. 23, 2015 (Jul. 23, 2015), pp. 259-270, XP037125212, ISSN: 0925-5710, DOI: 10.1007/S12185-015-1837-6.
International Search Report and Written Opinion for App. No. PCT/US2020/014940, dated Oct. 8, 2020, 15 pages.
Musah et al., "Inhibition of chlorine-induced airway fibrosis by budesonide", Toxicology and Applied Pharmacology, Academic Press, Amsterdam, NL, vol. 363, Sep. 3, 2018 (Sep. 3, 2018), pp. 11-21, XP085567595, ISSN: 0041-008X, DOI: 10.1016/J.TAAP. 2018.08.024.

* cited by examiner

TP17-JNJ-01: Fibrosis Scores (Day 70)

|  | A#1 | A#2 | A#3 | A#4 | A#5 | A#6 | A#7 | A#8 | A#9 | A#10 | Average |
|---|---|---|---|---|---|---|---|---|---|---|---|
| Gp1 (Veh/Veh) | 0 | 0 | 1 | 0 | 0 | 0 | NA | NA | NA | NA | 0.17 |
| Gp2 (NM/Veh) | 2 | 5 | 5 | 5 | 6 | 3 | 5 | 5 | 3 | FD | 4.33 |
| Gp3 (NM/2xTPOm) | 2 | 1 | 2 | 2 | 1 | 3 | 2 | MD | 2 | 4 | 2.11 |
| Gp4 (NM/3xTPOm) | 2 | 1 | 1 | 2 | 2 | 1 | 2 | MD | 4 | 2 | 1.89 |

NA: Not Applicable / Control Group consisted of 6 rats
FD: Found Dead after MRI scanning on Day 42
MD: MisDosed recorded and confirmed based the volume of Day 3 edema / Animal excluded from study Fibrosis Score
0 = Zero or infrequent blemishes observed in lung parenchyma that appear to be associated with blood vessels or normal airway structures
1 = Diffuse mottling exhibiting variegated shades of grey throughout one or both lung lobes
2 = Diffuse (spot) opacities within one or both sides of the lung
3 = Zonal punctate opacities predominantly within one side of the lung
4 = Zonal punctate opacities within both sides of the lung
5 = Numerous punctate opacities distributed throughout both sides of the lung
6 = Punctate opacities heavily distributed throughout both sides of the lung

FIGURE 5A

CT-scans of PTA-Processed Lungs

PTA Score 0
(Veh/Veh)

PTA Score 2
(Example: NM/TPOm)

PTA Score 5
(Example: NM/Veh)

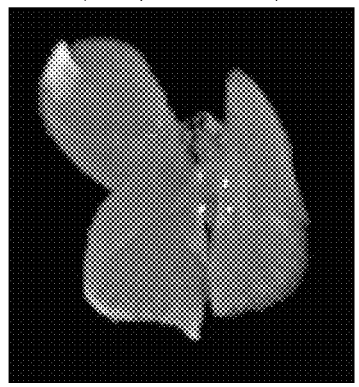

FIGURE 5B

METHODS OF MITIGATING TOXIC EFFECTS OF VESICANTS AND CAUSTIC GAS

CROSS REFERENCE TO RELATED APPLICATION

This application claims the benefit of U.S. patent application No. 62/796,754, filed Jan. 25, 2019, the disclosure of which is hereby incorporated by reference herein in its entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing for 688097.0958/457U1", creation date of Jan. 17, 2020, and having a size of about 3.6 kb. The sequence listing submitted via EFS-Web is part of the specification and is herein incorporated by reference in its entirety.

FIELD OF THE INVENTION

This application relates to methods and kits of mitigating a toxic effect of at least one of vesicants and caustic gases in a subject in need thereof. In particular, this application relates to methods comprising administering to the subject an effective amount of a thrombopoietin (TPO) mimetic, as well as kits comprising a pharmaceutical composition comprising an effective amount of a TPO mimetic and a pharmaceutically acceptable carrier.

BACKGROUND OF THE INVENTION

Military strategists that coordinate chemical threat preparedness anticipate an increasing risk for acts of terrorism involving the use of vesicants and caustic gases. The low technical skill and inexpensive reagents and equipment required to produce these substances increase the likelihood of use by radical groups conducting terror attacks on the homeland and battlefield.

Inhalation exposure to vesicant and caustic gases is known to induce acute lung injury marked by edema, micro-hemorrhage, cellular influx and endothelial/epithelial cell damage. In a small proportion of recorded human cases of exposures, the levels of toxic gas were high enough to results in death within a short period. However, for the much larger percentage of survivors of exposure incidents, the debilitating acute effects gradually subside with a concomitant development of a profibrotic process that leads to an irreversible pulmonary fibrosis contributing to long-term morbidity.

Although personal protection equipment (i.e., gas masks) can be used to prevent exposure, and specific types of counteragents are being developed to neutralize these reactive substances following release into the environment, there are limited options to mitigate the toxic effects of these substances immediately following human exposure.

For example, U.S. Patent Application Publication No. 2003/0083321 discloses compositions and methods for minimizing or avoiding adverse effects of vesicants such as mustard gas and other agents that cause vesication-type reactions. The compositions comprise at least one matrix metalloproteinase inhibitor, preferably in combination with at least one protease inhibitor.

International Patent Application Publication No. WO 2014028509 disclosed a method of treating a subject having a bone marrow injury resulting from exposure to mustard gas and nitrogen mustard. The method involves administering a c-Mpl receptor agonist, such as thrombopoietin (TPO) mimetics. International Patent Application Publication No. WO 2008/086025 also discloses a method of treating a respiratory disorder by administering compounds having erythropoietin activity or thrombopoietin (TPO) activity.

It is known that TPO regulates platelet levels by binding to c-MPL on megakaryocytes (to stimulate platelet maturation) and existing platelets (providing negative feedback) (Mitchell and Bussell, Semin. Hematol. 52(1):46-52 (2015)). TPO may also act directly on vasculature by binding to c-mpl receptors located on vascular endothelial cells (Langer et al., J. Mol. Cell Cardiol. 47(2):315-25 (2009)). There have been several studies demonstrating direct vascular protective effects of thrombopoietin in animal models of doxorubicin mediated cardiovascular injury (Chan et al., Eur. J. Heart Fail. 13(4):366-76 (2011)), cardiovascular ischemia reperfusion injury (Baker et al., Cardiovasc. Res. 77(1):44-53 (2008)) and stroke (Zhou et al., J. Cereb Blood Flow Metab. 31(3):924-33 (2011)). However, recombinant human TPO (rhTPO) is not a viable therapy in humans, due to induction of cross-reactive antibodies to endogenous TPO that can lead to chronic thrombocytopenia (Li et al., Blood 98(12):3241-8 (2001)).

There is a need for new ways to mitigate the toxic effects of the vesicants and caustic gases following human exposure.

BRIEF SUMMARY OF THE INVENTION

It is now discovered that thrombopoietin (TPO) mimetics has a significant mitigating effects on numerous endpoints of vesicant induced damages. Many of these endpoints are associated with the ability of TPO mimetics to function as a vascular protectant.

Accordingly, in one general aspect, the application relates to a method of mitigating a toxic effect of at least one of vesicants and caustic gases in a subject exposed to the vesicant or caustic gas. The method comprises administering to the subject in need thereof an effective amount of a thrombopoietin (TPO) mimetic, preferably the TPO mimetic comprises the amino acid sequence of SEQ ID NO:1, more preferably the TPO mimetic is RWJ-800088 or romiplostim.

In certain embodiments, the subject is in need of mitigating a toxic effect of a vesicant. The vesicant can, for example, be selected from a group consisting of distilled mustard, mustard gas, mustard/lewisite, mustard/T, nitrogen mustard, sesqui mustard, sulfur mustard, phosgene oxime, cantharidin, and furanocoumarin.

In certain embodiments, the subject is in need of mitigating a toxic effect of a caustic gas. The caustic gas can, for example, be selected from a group consisting of hydrogen sulfide, hydrogen fluoride, hydrogen chloride, hydrogen bromide, hydrogen cyanide, arsine, phosphine, nitric oxide, nitrogen dioxide, sulfur dioxide, ozone, chlorine, methylamine and ammonia.

In certain embodiments, the toxic effect is one or more selected from the group consisting of vascular damage, micro-hemorrhage, cellular influx, pulmonary fibrosis, mortality, and morbidity, wherein the toxic effect is induced by at least one of the vesicant and the caustic gas. Preferably, the toxic effect is lung micro-hemorrhage.

Acute Lung Injury and Acute Respiratory Distress Syndrome have a pathogenesis that relates to the generation of reactive oxygen species that are similar to what are generated with vesicants and chemical toxicants in the lung. Similar to chemical injury, excessive generation of oxygen radicals under pathological conditions such as acute lung injury (ALI) and its most severe form acute respiratory distress syndrome (ARDS) leads to increased endothelial permeability, loss of junctional integrity of vascular micro vessels and migration of solutes and fluids in the alveolar lumen. Accordingly, this disclosure provides a method of mitigating a toxic effect of oxidative stress in a subject in need thereof, the method comprising administering to the subject an effective amount of a TPO mimetic. Also disclosed is a method of mitigating a toxic effect of endothelial injury in a subject in need thereof, the method comprising administering to the subject an effective amount of a TPO mimetic. Yet another embodiment provided is a method of mitigating the toxic effects of oxidative stress and endothelial injury in a subject in need thereof, the method comprising administering to the subject an effective amount of a TPO mimetic. The provided methods of oxidative stress or endothelial injury includes administering to the subject in need thereof an effective amount of a TPO mimetic, which in some embodiments, may have the amino acid sequence of SEQ ID NO:1; the TPO mimetic could alternatively be RWJ-800088; the administered TPO mimetic could also be romiplostim.

As provided herein, the described TPO mimetic, such as RWJ-800088 or romiplostim, can be administered to a subject to mitigate toxic effects associated with exposure to a chemical vesicant or caustic gas.

In another general aspect, the application relates to a kit of mitigating a toxic effect of at least one of vesicants and caustic gases in a subject exposed to the vesicant or caustic gas. The kit comprises a pharmaceutical composition comprising an effective amount of a TPO mimetic and a pharmaceutically acceptable carrier, and at least one additional therapeutic agent or device for mitigating vesicant injury. Optionally, the kit further comprises a tool for administering the TPO mimetic to the subject. Preferably, the kit comprises a TPO mimetic having the amino acid sequence of SEQ ID NO:1, more preferably the TPO mimetic of RWJ-800088 or romiplostim.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 1A shows the RBC content and FIG. 1B shows the WBC content, indicating that TPOm administration decreases the micro-hemorrhage and WBC influx into the airspace of the lung induced by NM exposure.

FIG. 2A shows the red color (shown as darker gray in B&W) of the BAL (indicative of RBC content) and 2B shows the optical density differences, which are also indicative of RBC content. FIG. 2C shows the WBC content, indicating that both romiplostim and TPOm administration decreases the micro-hemorrhage and WBC influx into the airspace of the lung induced by NM exposure.

FIG. 3A shows the lungs from rats in the vehicle control group reflecting blood contained in the pulmonary vasculature, while FIG. 3B shows the lungs of rats exposed to NM exhibiting numerous sites of sub-plural micro-hemorrhage (arrows) surrounded by reduced perfusion. FIG. 3C shows that the severity and number of micro-hemorrhage sites were markedly reduced compared to rats treated with NM alone (FIG. 3B). These results indicate that TPOm prevents severe vascular damage associated with the development of micro-hemorrhage and cellular influx following NM exposure.

FIGS. 5A and 5B show effect of TPOm on NM-induced pulmonary fibrosis. In extended chronic studies examining the effect of TPOm on the development of lung fibrosis, rats received multiple doses of TPOm (2 or 3 doses) following treatment with the NM vesicant. Mill was then conducted periodically throughout an extended post-exposure period to evaluate levels of pulmonary edema. At 70-day post exposure, the lungs of rats were inflation-fixed in situ to maintain natural pulmonary volumes. The lungs were then excised, fixed overnight in formalin and processed for ex vivo microCT imaging by equilibration with phosphotungstic acid (PTA), a microCT radiographic contrast agent that exhibits a high binding affinity for collagen. This PTA processing method enables the quantitation and visualization of the fibrosis developing in the lung in 2- and 3-dimensions. Following microCT scanning, the lungs were transferred to 70% ethanol for 4 days to remove the Phosphotungstic Acid (PTA) and processed for histological evaluation. FIG. 5A tabulates the data showing TPOm significantly decreased numerous elements of the fibrotic condition in NM-exposed lung (fibrosis score of 2.11 and 1.89 for TPOm treated vs. 4.33 for vehicle control). FIG. 5B shows the grey-scale CT images representing the radiodensity of PTA-treated lungs, indicating that TPOm reduced the number and altered the distribution of collagen-containing fibrotic lesions in the lungs of NM-exposed rats that appear as punctate light-grey foci distributed throughout the lung.

FIG. 6 demonstrates that TPOm administration following NM exposure could prolong life and resulted in fewer deaths. The reduction in body weight was greater for the NM/Veh compared to the NM/TPOm treatment groups with a marked (5% to 7%, ~20 gram) weight loss protection associated with TPOm treatment, which also suggests a mitigating effect of this agent on morbidity.

DETAILED DESCRIPTION OF THE INVENTION

Figure 1A:
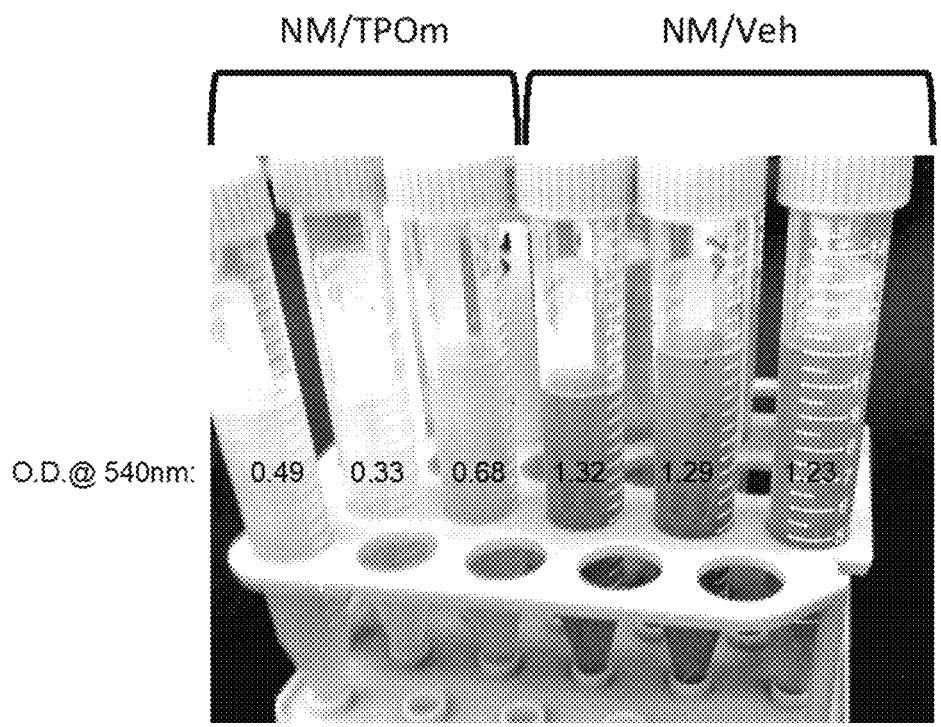
FIGS. 1A and 1B show the effects of TPOm treatment on hemorrhage as evaluated by optical density of the Broncho-Alveolar Lavage (BAL) and WBC counts in the BAL. In the studies, groups of male Wistar rats received the nitrogen mustard (NM). Six hours later, the rats were treated with either vehicle or TPOm. On day 3, MRI scans were conducted on the rats using FSE (T2-weighted) sequences to characterize the extent of the pulmonary edema induced by NM exposure. Following imaging, rats were euthanized and the lungs were lavaged with PBS and the levels of red blood cell (RBC), white blood cell (WBC), and the concentration of the pro-fibrogenic factor, transforming growth factor beta 1(TGF-1b), in the Broncho-Alveolar Lavage (BAL) fluid were determined using standard methodologies.

This disclosure is based upon, at least in part, on the identification of a thrombopoietin (TPO) mimetic as a therapeutic for mitigating a toxic effect of at least of one vesicants and caustic gases in a subject in need thereof. The TPO mimetic can be formulated and administered to the subject who is or will be exposed to the vesicant or caustic gas to protect against the toxic effects.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human, who will be or has been treated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right", "left", "lower" and "upper" designate directions in the drawings to which reference is made.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The term "toxic effect," as used herein, refers to the acute and/or chronic toxicity of a vesicant or a caustic gas in a subject following exposure to the vesicant or the caustic gas. The term "toxic effect" can refer to, but are not limited to: edema, vascular damage, micro-hemorrhage such as lung micro-hemorrhage, cellular influx, endothelial/epithelial cell damage, or pulmonary fibrosis. The term "toxic effect" can also be mortality or morbidity.

The term "a vesicant," as used herein, refers to a chemical compound that is toxic and typically causes long lasting damage to tissues in contact with or surrounding the compound. A vesicant can cause severe skin, eye and mucosal pain and irritation. Examples of vesicants include, but are not limited to, distilled mustard, mustard gas, lewisite, mustard/lewisite, mustard/T, nitrogen mustard, sesqui mustard, sulfur mustard, phosgene oxime, cantharidin, or furanocoumarin. Vesicants can also include blister agents, named for their ability to cause severe chemical burns, resulting in painful water blisters on the bodies of those affected.

Most vesicants fall into one of three groups: sulfur mustards, a family of sulfur-based agents, including mustard gas; nitrogen mustards, a family of agents similar to the sulfur mustards, but based on nitrogen instead of sulfur; lewisite, an early vesicant that was developed, but not used, during World War I. Phosgene oxime, also termed a nettle agent (urticant), is also included among the vesicants. Although the term of "vesicant" is often used in connection with large-scale burns caused by chemical spills or chemical warfare agents, some naturally occurring substances such as cantharidin are also blister-producing agents (vesicants). Furanocoumarin, another naturally occurring vesicant, can also cause vesicant effects indirectly, for example, by greatly increasing skin photosensitivity.

The term "a caustic gas," as used herein, refers to a gas capable of causing burning or corroding body tissues on contact by a chemical reaction. Examples of caustic gas include, but are not limited to, hydrogen sulfide, hydrogen fluoride, hydrogen chloride, hydrogen bromide, hydrogen cyanide, arsine, phosphine, nitric oxide, nitrogen dioxide, sulfur dioxide, ozone, chlorine, methylamine, or ammonia. Caustic gases can have the ability to burn or corrode body tissues on contact by chemical reactions. In general, there are three types of caustic gases: acidic gases, basic gases, and oxidizing gases.

The term "additional therapeutic agent," as used herein, refers to any compound or therapeutic agent known to or that demonstrates advantageous properties when administered with TPO or a TPO mimetic. Examples of such agents can include, but are not limited to, analgesics, antiseptics, other TPO mimetics, other cytokines, soluble mpl receptors, hematopoietic factors, interleukins, growth factors or antibodies, and chemotherapeutic agents. The other cytokines can be stem cell factor (SCF), interleukin 3 (IL-3), or Flt-3 ligand. Ku et al., Blood, 87:4544-4551 (1996); Sitnicka et al., Blood, 87:4998-5005 (1996). In particular, the additional therapeutic agents can be atropine, atropine sulfate, homatropine, narcotic analgesics, or N-acetylcysteine (NAC).

TPO Mimetic

As used herein, a "TPOm", "TPO mimetic" or "thrombopoietin mimetic" refers to a compound comprising a peptide capable of binding to and activating a thrombopoietin receptor. Preferably, in a TPO mimetic useful for the invention, the peptide capable of binding to and activating a thrombopoietin receptor has no significant homology with thrombopoietin (TPO). The lack of homology with TPO reduces the potential for generation of TPO antibodies. Examples of such peptide useful in a TPO mimetic include, but are not limited to, those described in U.S. Publication Nos. 2003/0158116; 2005/0137133; 2006/0040866; 2006/0210542; 2007/0148091; 2008/0119384; U.S. Pat. Nos. 5,869,451; 7,091,311; 7,615,533; 8,227,422; International Patent Publications WO2007/021572; WO2007/094781; and WO2009/148954, the entire contents of which are incorporated herein by reference. More preferably, in a TPO mimetic useful for the invention, the peptide capable of binding to and activating a thrombopoietin receptor is covalently linked to a moiety that improves one or more properties of the peptide. By way of a non-limiting example, the moiety can be a hydrophilic polymer, including but not limited to polyethylene glycol (PEG), polypropylene glycol, polylactic acid and polyglycolic acid. The moiety can also be a polypeptide, such as a Fc region or an albumin.

In a preferred embodiment, a TPO mimetic useful for the invention comprises a peptide having the amino acid sequence of: IEGPTLRQXaaLAARYaa (SEQ ID NO:1), wherein Xaa is tryptophan (W) or β-(2-naphthyl)alanine (referred to herein as "2-Nal"), and Yaa is alanine (A) or sarcosine (referred herein as "Sar"). Preferably, the peptide of SEQ ID NO:1 is covalently linked to a PEG or fused to a Fc domain.

In some embodiments, a TPO mimetic useful for the invention comprises a peptide of SEQ ID NO:1 covalently linked to a PEG, preferably a PEG having an average molecular weight of between about 5,000 to about 30,000 Daltons. Preferably, the PEG is selected from the group consisting of monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), and monomethoxypolyethylene glycol-imidazolyl-carbonyl (MePEG-IM). The PEGylation of the peptide leads to a reduced clearance of the compound without loss of potency. See, e.g., U.S. Pat. No. 7,576,056, the entire contents of which are incorporated herein by reference.

In one preferred embodiment, a TPO mimetic useful for the invention is RWJ-800088 or a derivative thereof. As used herein, "RWJ-800088" refers to a 29-mer peptide having two identical 14-mers linked (SEQ ID NO:2) by a lysinamide residue as follows:

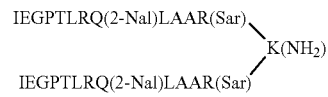

and having a methoxypoly(ethylene glycol) (MPEG) covalently linked to each N-terminal isoleucine, or a pharmaceutically acceptable salt or ester thereof. The RWJ-800088 is thus composed of two 14 amino acid peptide chains of SEQ ID NO:1, where Xaa is 2-Nal and Yaa is Sar, linked by lysinamide reside, and each N-terminal isoleucine is linked to a methoxy polyethylene glycol (MPEG) chain. Accordingly, RWJ-800088 has an abbreviated molecular structure of (MPEG-Ile-Glu-Gly-Pro-Thr-Leu-Arg-Gln-(2-Nal)-Leu-Ala-Ala-Arg-(Sar))$_2$-Lys-Nth; wherein (2-Nal) is Beta-(2-naphthyl)alanine, (Sar) is sarcosine and MPEG is methoxypoly(ethylene glycol), or a pharmaceutically acceptable salt or ester thereof. Preferably, the MPEG has an approximately 20,000 Dalton molecular weight or represents methoxypolyethylene glycol20000.

In one embodiment, RWJ-800088 has a molecular structure of formula (I), or a pharmaceutically acceptable salt or ester thereof:

```
                                                          (SEQ ID NO: 4)
MDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQ

GNVFSCSVMHEALHNHYTQKSLSLSPGKGGGGGIEGPTLRQWLAARAGGG

GGGGGIEGPTLRQWLAARA,
```

It has the thrombopoietin receptor binding domain amino acid sequence of IEGPTLRQWLAARA (SEQ ID NO:3).

Formula (I)

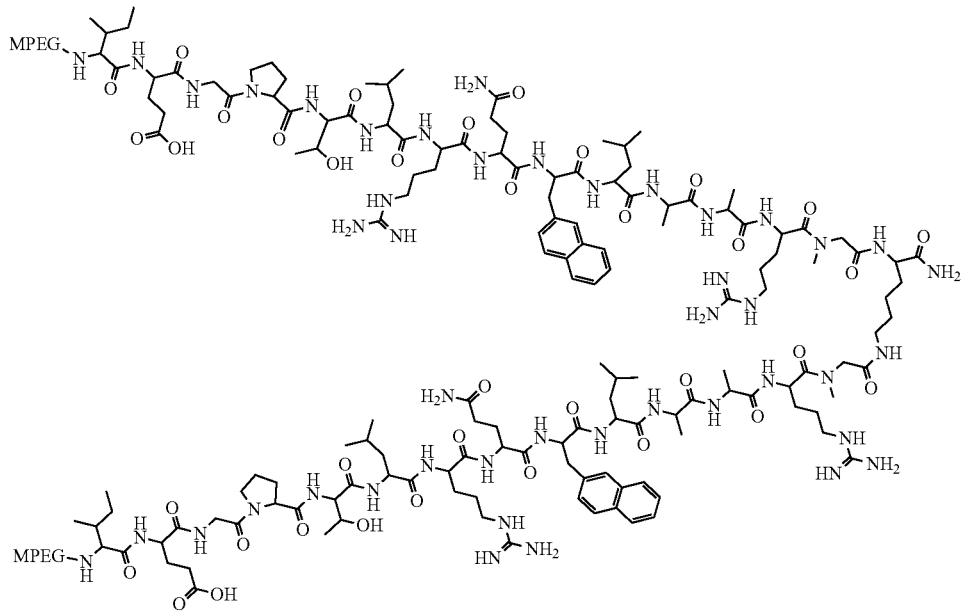

In a preferred embodiment, the MPEG in RWJ-800088 is methoxypolyethyleneglycol20000, and the RWJ-800088 has the full chemical name of: methoxypolyethyleneglycol20000-propionyl-L-Isoleucyl-L-Glutamyl-Glycyl-L-Prolyl-L-Threonyl-L-Leucyl-L-Arginyl-L-Glutaminyl-L-2-Naphthylalanyl-L-Leucyl-L-Alanyl-L-Alanyl-L-Arginyl-Sarcosyl-Nε-(methoxypolyethyleneglycol20000-propionyl-L-Isoleucyl-L-Glutamyl-Glycyl-L-Prolyl-L-Threonyl-L-Leucyl-L-Arginyl-L-Glutaminyl-L-2-Naphthylalanyl-L-Leucyl-L-Alanyl-L-Alanyl-L-Arginyl-Sarcosyl-)-Lysinamide, or a pharmaceutically acceptable salt or ester thereof. The molecular weight of the peptide without PEG is 3,295 Daltons and with two 20,000 Dalton MPEG chains is approximately 43,295 Daltons.

In some embodiments, a TPO mimetic useful for the invention comprises a peptide of SEQ ID NO:1 fused to a Fc domain. Fusing the peptide to a Fc domain can stabilize the peptide in vivo. See, e.g., U.S. Pat. No. 6,660,843, the entire contents of which are incorporated herein by reference.

In another preferred embodiment, a TPO mimetic useful for the invention is romiplostim. As used herein, "romiplostim" refers to fusion protein having a Fc domain linked to the N-terminal isoleucine of the peptide of SEQ ID NO:1, where Xaa is W and Yaa is A. In particular, romiplostim has the following amino acid sequence:

Dosage and Administration

In the instant invention, the inventors discovered that TPO mimetics have significant mitigating effects on toxic effects of vesicants or caustic gases following human exposure. Thus, methods of the invention comprise administering to a subject in need thereof an effective amount of a TPO mimetic to thereby achieve mitigation on one or more acute and chronic endpoints of NM-induced lung injury, such as vascular damage, pulmonary hemorrhage, influx of inflammatory cells into lung air spaces, accumulation of profibrotic cytokines in the lung, the development of pulmonary fibrosis, vesicant-induced edema, vesicant-induced mortality and morbidity, in the subject in need thereof, such as a subject exposed to a vesicant, or a subject exposed to a caustic gas.

The TPO mimetic can, for example, be administered as an active ingredient of a pharmaceutical composition in association with a pharmaceutical carrier or diluent. The TPO mimetics can be administered by oral, pulmonary, parental (intramuscular (IM), intraperitoneal (IP), intravenous (IV) or subcutaneous injection (SC)), inhalation (via a fine powder formulation), transdermal, nasal, vaginal, rectal, or sublingual routes of administration can be formulated in dosage forms appropriate for each rout of administration. For example, International Publication No. WO1993/25221 (Bernstein et al.) discloses biodegradable polymer microspheres containing erythropoietin (EPO), which can be administered topically, locally or systemically by parenteral administration or enteral administration, preferably oral administration. WO1994/17784 (Pitt et al.) discloses that EPO can be administered systemically via pulmonary route and that such delivery results in comparable levels of therapeutic benefit as compared with other EPO administration methods. Similar compositions and methods can be used for the administration of TPO mimetic of the present disclosure.

Solid dosage forms for oral administration include capsules, tablets, pills, powders, and granules. In such solid dosage forms, the active peptide compound is admixed with at least one pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations for parental administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They may be sterilized by, for example, filtration through bacteria retaining filter, by incorporating sterilizing agents into the compositions, by irradiating the compositions, or by heating the compositions. They can also be manufactured using sterile water, or some other sterile injectable medium immediately before use.

Administration of the TPO mimetic is typically intramuscular, subcutaneous, or intravenous. However other modes of administration such as cutaneous, intradermal or nasal can be envisaged as well. Intramuscular administration of the TPO mimetic can be achieved by using a needle to inject a suspension of the TPO mimetic composition. An alternative is the use of a needleless injection device to administer the composition (using, e.g., Biojector™) or a freeze-dried powder of the TPO mimetic composition.

For intravenous, cutaneous or subcutaneous injection, or injection at the site of affliction, the TPO mimetic composition can be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, and Lactated Ringer's Injection. Preservatives, stabilizers, buffers, antioxidants and/or other additives can be included, as required. A slow-release formulation can also be employed.

Compositions for rectal or vaginal administration are preferably suppositories that may contain, in addition to the active TPO mimetic, excipients such as cocoa butter or a suppository wax. Compositions for nasal or sublingual administration are also prepared with standard excipients well known in the art.

Typically, administration will have a therapeutic and/or prophylactic aim to mitigate the toxic effects of vesicants or caustic gases in a subject prior to, during or following the exposure thereof. In therapeutic applications, the TPO mimetic compositions are administered to a subject during or after the exposure to a vesicant or caustic gas, and the TPO mimetic compositions are administered in an amount sufficient to cure or at least partially provide mitigation for the toxic effects. In prophylactic applications, TPO mimetic compositions are administered to a subject susceptible to, or at risk of, an exposure to a vesicant or caustic gas prior to such exposure. In each of these scenarios the amount of the TPO mimetic compositions will depend on the state and nature of the exposure (e.g., category and concentration of the vesicant or caustic gas, length of exposure) and the physical characteristics of the subject (e.g., height, weight, etc.).

The pharmaceutically acceptable compositions containing the TPO mimetic are administered to a subject, giving rise to mitigating the toxic effect of the vesicant or toxic gas in the subject. An amount of a composition sufficient to mitigate the toxic effect is defined to be an "effective dose" or an "effective amount" of the composition.

An effective amount of the TPO mimetic administered to a subject for the methods provided herein can vary based on the subject in question. The species differences in potency has been described for other TPO mimetics in the literature and is attributed to differences in receptor affinity (Erickson-Miller C L, et al. "Discovery and characterization of a selective, non-peptidyl thrombopoietin receptor agonist," Exp. Hematol., 2005; 33:85-93 and Nakamura T, et al. "A novel non-peptidyl human c-Mpl activator stimulates human megakaryopoiesis and thrombopoiesis," Blood. 2006; 107:4300-7). Accordingly, in some embodiments an effective amount of TPO mimetic may be an amount from 0.1 microgram (µg) to 6 µg, per kg body weight of a subject. In a further embodiment, an effective amount of TPO mimetic may be an amount from 2.25 µg to 4 µg, of the TPO mimetic per kg body weight of a subject. For certain subjects, an effective amount of TPO mimetic may be an amount from 0.1 milligram (mg) to 6 mg, per kg body weight of a subject. In a further embodiment, an effective amount of TPO mimetic may be an amount from 2.25 mg to 4 mg, of the TPO mimetic per kg body weight of a subject. Still in other subjects, an effective amount of TPO mimetic may be an amount from 6 mg to 60 mg, per kg body weight of a subject. In a further embodiment, an effective amount of TPO mimetic may be an amount from 20 mg to 40 mg, of the TPO mimetic per kg body weight of a subject.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of category and concentration of the vesicant or caustic gas, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980. Based on the dosing ranges described herein, the specific dosing examples provided, and the understanding that different species may require dosing adjustments based on receptor sensitivity, those skilled in the art will be able to determine an effective dosage for the subject in question.

In certain embodiments, the subject is administered one dose of the effective amount of the TPO mimetic.

In certain embodiments, the subject is administered multiple doses of the effective amount of the TPO mimetic.

Following production of the TPO mimetic and optional formulation of the TPO mimetic into compositions, the compositions can be administered to an individual, particularly human or other primate. Administration can be to humans, or another mammal, e.g., mouse, rat, hamster, guinea pig, rabbit, sheep, goat, pig, horse, cow, donkey, monkey, dog or cat. Delivery to a non-human mammal need not be for a therapeutic purpose, but can be for use in an experimental context, for instance in investigation of mechanisms of protecting vascular integrity due to administration of the TPO mimetic.

The TPO mimetic compositions of the invention can be administered alone or in combination with other treatments, either simultaneously or sequentially dependent upon the condition to be treated.

The TPO mimetic compositions can, if desired, be presented in a kit, pack or dispenser, which can contain one or more unit dosage forms containing the active ingredient. The kit, for example, can comprise metal or plastic foil, such as a blister pack. The kit, pack, or dispenser can be accompanied by instructions for administration. The kit can further comprise at least one additional therapeutic agent or a device for mitigating the toxic effect.

The additional therapeutic agent included in the kit refers to any compound or therapeutic agent known to or that demonstrates advantageous properties when administered with TPO or a TPO mimetic. Examples of such agents can be, but are not limited to: analgesics, antiseptics, other TPO mimetics, other cytokines, soluble mpl receptors, hematopoietic factors, interleukins, growth factors or antibodies, and chemotherapeutic agents. The other cytokines can be stem cell factor (SCF), interleukin 3 (IL-3), or Flt-3 ligand. Ku et al., Blood, 87:4544-4551 (1996); Sitnicka et al., Blood, 87:4998-5005 (1996).

The device included in the kit can be, for example, a container, a delivery vehicle, or an administration device.

EMBODIMENTS

The invention provides also the following non-limiting embodiments.

Embodiment 1 is a method of mitigating a toxic effect of:
(i) at least one of a vesicant and a caustic gas in a subject in need thereof, the method comprising administering to the subject an effective amount of a thrombopoietin (TPO) mimetic, wherein the administration of the effective amount of the TPO mimetic to the subject mitigates the toxic effect of the at least one of the vesicant and the caustic gas; or
(ii) oxidative stress or endothelial injury in a subject in need thereof, the method comprising administering to the subject an effective amount of a TPO mimetic, wherein the administration of the effective amount of the TPO mimetic to the subject mitigates the toxic effect oxidative stress or endothelial injury.

Embodiment 1(a) is the method of embodiment 1, wherein the TPO mimetic comprises a peptide having the amino acid sequence of SEQ ID NO:1.

Embodiment 1(b) is the method of embodiment 1(a), wherein the peptide has the amino acid sequence of SEQ ID NO:2.

Embodiment 1(c) is the method of embodiment 1(a) or 1(b), wherein the TPO mimetic further comprises a hydrophilic polymer covalently linked to the peptide.

Embodiment 1(d) is the method of embodiment 1(c), wherein the hydrophilic polymer is any one of: i) polyethylene glycol (PEG), ii) polypropylene glycol, iii) polylactic acid, or iv) polyglycolic acid.

Embodiment 1(e) is the method of embodiment 1(d), wherein the hydrophilic polymer is PEG.

Embodiment 1(f) is the method of embodiment 1(e), wherein the PEG is any one of monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), or monomethoxypolyethylene glycol-imidazolyl-carbonyl (MePEG-IM).

Embodiment 1(g) is the method of embodiment 1(e), wherein the PEG is methoxypoly(ethylene glycol) (MPEG).

Embodiment 1(h) is the method of embodiment 1(g), wherein the TPO mimetic is RWJ-800088 having a molecular structure of formula (I).

Embodiment 1(h)(1) is the method of embodiment 1(g), wherein the TPO mimetic is RWJ-800088 having a molecular structure of formula (I), or a pharmaceutically acceptable salt or ester thereof.

Embodiment 1(i) is the method of embodiment 1(h) or 1(h)(1), wherein the MPEG in the RWJ-800088 is methoxypolyethylene glycol20000.

Embodiment 1(j) is the method of embodiment 1(a), wherein the peptide has the amino acid sequence of SEQ ID NO:3.

Embodiment 1(k) is the method of embodiment 1(j), wherein the peptide is fused to a polypeptide.

Embodiment 1(l) is the method of embodiment 1(k), wherein the polypeptide is a Fc domain.

Embodiment 1(m) is the method of embodiment 1(l), wherein the TPO mimetic is romiplostim.

Embodiment 1(m)(1) is the method of embodiment 1(m), wherein romiplostim comprises the amino acid sequence of SEQ ID NO:4.

Embodiment 2 is the method of any one of embodiments 1-1(m)(1), wherein the TPO mimetic is administered to the subject before the subject is exposed to the at least one of the vesicant and the caustic gas.

Embodiment 3 is the method of any one of embodiments 1-1(m)(1), wherein the TPO mimetic is administered to the subject after the subject is exposed to the at least one of the vesicant and the caustic gas.

Embodiment 4 is the method of any one of embodiments 1-1(m)(1), wherein the TPO mimetic is administered to the subject while the subject is exposed to the at least one of the vesicant and the caustic gas.

Embodiment 5 is the method of any one of embodiments 1 to 4, wherein the vesicant is selected from the group consisting of distilled mustard, mustard gas, lewisite, mustard/lewisite, mustard/T, nitrogen mustard, sesqui mustard, sulfur mustard, phosgene oxime, cantharidin, and furanocoumarin.

Embodiment 6 is the method of any one of embodiments 1 to 5, wherein the caustic gas is selected from the group consisting of hydrogen sulfide, hydrogen fluoride, hydrogen chloride, hydrogen bromide, hydrogen cyanide, arsine, phosphine, nitric oxide, nitrogen dioxide, sulfur dioxide, ozone, chlorine, methylamine, and ammonia.

Embodiment 7 is the method of any one of embodiments 1 to 6, wherein the subject is in need of mitigating a toxic effect of at least one of a vesicant and a caustic gas, wherein the vesicant is selected from the group consisting distilled mustard, mustard gas, lewisite, mustard/lewisite, mustard/T, nitrogen mustard, sesqui mustard, sulfur mustard, phosgene oxime, cantharidin, and furanocoumarin; and wherein the caustic gas is selected from the group consisting of hydrogen sulfide, hydrogen fluoride, hydrogen chloride, hydrogen bromide, hydrogen cyanide, arsine, phosphine, nitric oxide, nitrogen dioxide, sulfur dioxide, ozone, chlorine, methylamine, and ammonia.

Embodiment 7(a) is the method of embodiment 7, wherein the subject is in need of mitigating a toxic effect of at least one vesicant.

Embodiment 7(b) is the method of embodiment 7, wherein the subject is in need of mitigating a toxic effect of at least one caustic gas.

Embodiment 7(c) is the method of embodiment 7, wherein the subject is in need of mitigating a toxic effect of at least two vesicants.

Embodiment 7(d) is the method of embodiment 7, wherein the subject is in need of mitigating a toxic effect of at least two caustic gases.

Embodiment 7(e) is the method of embodiment 7, wherein the subject is in need of mitigating a toxic effect of at least three or more vesicants.

Embodiment 7(f) is the method of embodiment 7, wherein the subject is in need of mitigating a toxic effect of at least three or more caustic gases.

Embodiment 8 is the method of any one of embodiments 1 to 7, wherein the effective amount of the TPO mimetic is based on the body weight of the subject.

Embodiment 8(a) is the method of any one of embodiments 1 to 7, wherein the effective amount of the TPO mimetic is within the range of 0.1 µg to 6 µg, per kg body weight of the subject.

Embodiment 8(b) is the method of any one of embodiments 1 to 7, wherein the effective amount of the TPO mimetic is within the range of 2.25 µg to 4 µg, per kg body weight of the subject.

Embodiment 8(c) is the method of any one of embodiments 1 to 7, wherein the effective amount of the TPO mimetic is within the range of 0.1 mg to 6 mg, per kg body weight of the subject.

Embodiment 8(d) is the method of any one of embodiments 1 to 7, wherein the effective amount of the TPO mimetic is within the range of 2.25 mg to 4 mg, per kg body weight of the subject.

Embodiment 8(e) is the method of any one of embodiments 1 to 7, wherein the effective amount of the TPO mimetic is within the range of 6 mg to 60 mg, per kg body weight of the subject.

Embodiment 9 is the method of any one of embodiments 1 to 8(a), wherein the toxic effect is one or more selected from the group consisting of vascular damage, pulmonary hemorrhage, influx of inflammatory cells into lung air spaces, accumulation of profibrotic cytokines in the lung, pulmonary fibrosis, pulmonary edema, mortality and morbidity, wherein the toxic effect is induced by the at least one of the vesicant and the caustic gas.

Embodiment 9(a) is the method of embodiment 9, wherein the toxic effect is vascular damage.

Embodiment 9(b) is the method of embodiment 9, wherein the toxic effect is pulmonary hemorrhage, preferably pulmonary micro-hemorrhage.

Embodiment 9(c) is the method of embodiment 9, wherein the toxic effect is influx of inflammatory cells into lung air spaces.

Embodiment 9(d) is the method of embodiment 9, wherein the toxic effect is accumulation of profibrotic cytokines in the lung.

Embodiment 9(e) is the method of embodiment 9, wherein the toxic effect is pulmonary fibrosis.

Embodiment 9(f) is the method of embodiment 9, wherein the toxic effect is pulmonary edema.

Embodiment 9(g) is the method of embodiment 9, wherein the toxic effect is mortality induced by the at least one of the vesicant and the caustic gas.

Embodiment 9(h) is the method of embodiment 9, wherein the toxic effect is morbidity induced by the at least one of the vesicant and the caustic gas.

Embodiment 10 is the method of any one of embodiments 1-9(h), wherein the effective amount of the TPO mimetic is administered to the subject by any one of intravenous, intramuscular, intracutaneous, or subcutaneous injection.

Embodiment 10(a) is the method of embodiment 10, wherein the effective amount of the TPO mimetic is administered to the subject by subcutaneous injection.

Embodiment 10(b) is the method of embodiment 10, wherein the effective amount of the TPO mimetic is administered to the subject by intravenous injection.

Embodiment 10(c) is the method of embodiment 10, wherein the effective amount of the TPO mimetic is administered to the subject by intramuscular injection.

Embodiment 10(d) is the method of embodiment 10, wherein the effective amount of the TPO mimetic is administered to the subject by intracutaneous injection.

Embodiment 11 is a kit for mitigating a toxic effect of at least one of a vesicant and a caustic gas in a subject in need thereof, comprising a pharmaceutical composition comprising an effective amount of a TPO mimetic and a pharmaceutically acceptable carrier.

Embodiment 11(a) is the kit of embodiment 11, wherein the TPO mimetic comprises a peptide having the amino acid sequence of SEQ ID NO:1.

Embodiment 11(b) is the kit of embodiment 11, wherein the peptide has the amino acid sequence of SEQ ID NO:2.

Embodiment 11(c) is the kit of embodiment 11 (a) or 11(b), wherein the TPO mimetic further comprises a hydrophilic polymer covalently linked to the peptide.

Embodiment 11(d) is the kit of embodiment 11, wherein the hydrophilic polymer is any one of polyethylene glycol (PEG), polypropylene glycol, polylactic acid and polyglycolic acid.

Embodiment 11(e) is the kit of embodiment 11(d), wherein the hydrophilic polymer is PEG.

Embodiment 11(f) is the kit of embodiment 11(e), wherein the PEG is any one of monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), or monomethoxypolyethylene glycol-imidazolyl-carbonyl (MePEG-IM).

Embodiment 11(g) is the kit of embodiment 11(e), wherein the PEG is methoxypoly(ethylene glycol) (MPEG).

Embodiment 11(h) is the kit of embodiment 11(g), wherein the TPO mimetic is RWJ-800088 having a molecular structure of formula (I), or a pharmaceutically acceptable salt or ester thereof.

Embodiment 11(i) is the kit of embodiment 11(h), wherein the MPEG in the RWJ-800088 is methoxypolyethylene glycol20000.

Embodiment 11(j) is the kit of embodiment 11(a), wherein the peptide has the amino acid sequence of SEQ ID NO:3.

Embodiment 11(k) is the kit of embodiment 11(j), wherein the peptide is fused to a polypeptide.

Embodiment 11(l) is the kit of embodiment 11(k), wherein the polypeptide is a Fc domain.

Embodiment 11(m) is the kit of embodiment 11(l), wherein the TPO mimetic is romiplostim.

Embodiment 11(m)(1) is the kit of embodiment 11(m), wherein romiplostim comprises the amino acid sequence of SEQ ID NO:4.

Embodiment 12 is the kit of any one of embodiments 11-11(m)(1), further comprising at least one additional therapeutic agent or device for mitigating the toxic effect.

Embodiment 13 is the kit of embodiment 12, wherein the additional therapeutic agent is selected from the group consisting of analgesics, antiseptics, other TPO mimetics, other cytokines, soluble mpl receptors, hematopoietic factors, interleukins, growth factors or antibodies, and chemotherapeutic agents.

EXAMPLES

Example 1: Effect of TPOm on NM-induced Lung Injury

Materials and Methods

Animals: Male Wistar rats (300-320 grams) were divided into 2 groups: NM/Veh, and NM/TPOm.

Nitrogen Mustard Exposure: In this study, mechlorethamine, a non-gaseous Nitrogen Mustard (NM), was used as a surrogate for sulfur mustard, to facilitate the exposure of laboratory animals to a vesicant agent and to reduce hazards to researchers. It is expected that information gained in these studies using NM can be directly applied to guide the design and define the endpoints of interest in proposed studies involving exposures of sulfur mustard gas. In particular, groups of male Wistar rats (300-320 grams) received 0.125 mg/kg of the sulfur mustard surrogate, mechlorethamine, via tracheal instillation on day 0.

TPOm synthesis and treatments: TPOm was synthesized by Janssen Pharmaceuticals as described previously (see, e.g., U.S. Pat. No. 7,576,056). TPOm was reconstituted in sterile saline, sterile filtered, aliquoted, and stored at −20 C until use. TPOm was administered as a single dose via sub-cutaneous injection (0.3 mg/kg) 6 hours after exposure to nitrogen mustard (NM). This dose was selected based on its effectiveness in rat whole body radiation studies where it produced a substantial survival benefit compared to placebo when administered at multiple time points.

Magnetic resonance imaging (MRI) measurements: On day 3, MRI scans were conducted on the rats using FSE (T2-weighted) sequences to characterize the extent of the pulmonary edema induced by NM exposure.

Broncho-Alveolar Lavage (BAL) measurements: Following MRI scanning, rats were euthanized and the lungs were lavaged with aliquots (3×5 ml) of PBS and the levels of red blood cell (RBC), white blood cell (WBC), and transforming growth factor beta 1(TGF-1b) in the Broncho-Alveolar Lavage (BAL) were determined using standard methodologies. In particular, the lavage volumes recovered from each rat were pooled and the RBC content was recorded by digital photography. BAL samples were mixed gently and the number of WBC in the samples was determined using standard trypan blue exclusion methodology and hemocytometer counting. The BAL collected from the various treatment groups was centrifuged and the concentration of TGF-1b was determined in the cell-free supernatant using a TGF-1b ELISA.

Gross organ pathology measurements: After rats were euthanized, the thoracic cavities were surgically opened, and the descending blood vessels were severed. The blood fluids exterior to the collapsed lungs were gently rinsed with PBS and blotted with a damp surgical pad. Without perfusing the lung vasculature with PBS, the lungs were digitally photographed.

Results

TPOm and Romiplostim Protect Against Micro-Hemorrhage and Cellular Influx Following NM Exposure.

Figure 1B:
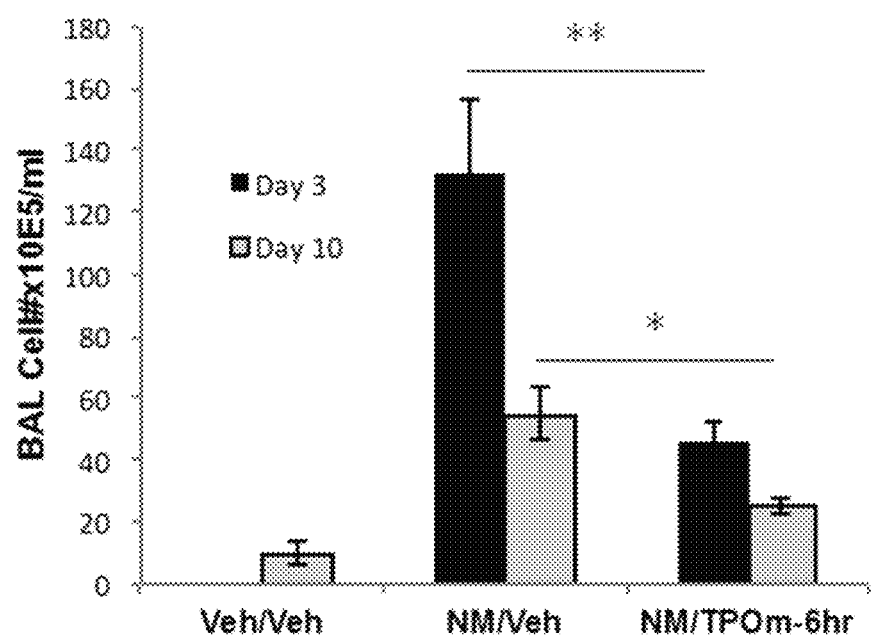
Figure 1C:
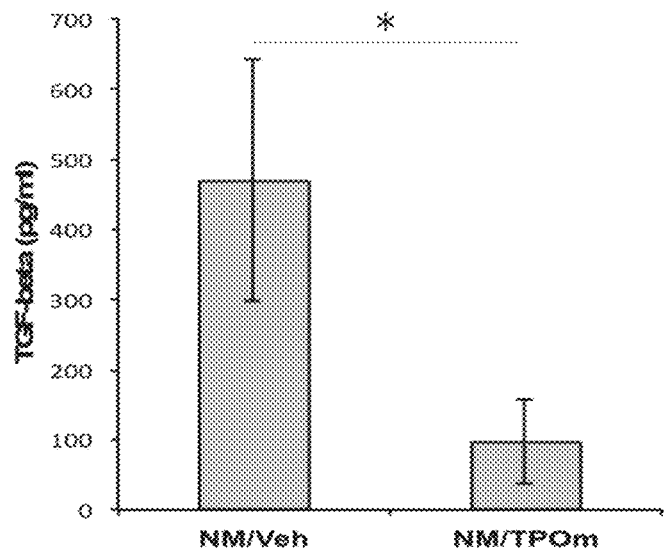
FIG. 1C shows the concentration of TGF-1b in the BAL fluid following treatment with NM+/−TPOm, indicating that TPOm reduced NM-induced elevation of TGF-1b (p<0.05).

The vascular protective effects of TPOm treatment (0.3 mg/kg, 6 h post NM-instillation) were observed in the cellular components of the Broncho-Alveolar Lavage (BAL). The RBC (FIG. 1A as measured by optical density) and WBC (FIG. 1B as measured by hemocytometer, p<0.05) content of the BAL, indicate that TPOm administration decreases the micro-hemorrhage and WBC influx into the airspace of the lung induced by NM exposure. TPOm was also found to reduce NM-induced elevations in the concentration of TGF-1b in the BAL fluid (FIG. 1C, p<0.05)

Figure 2A:
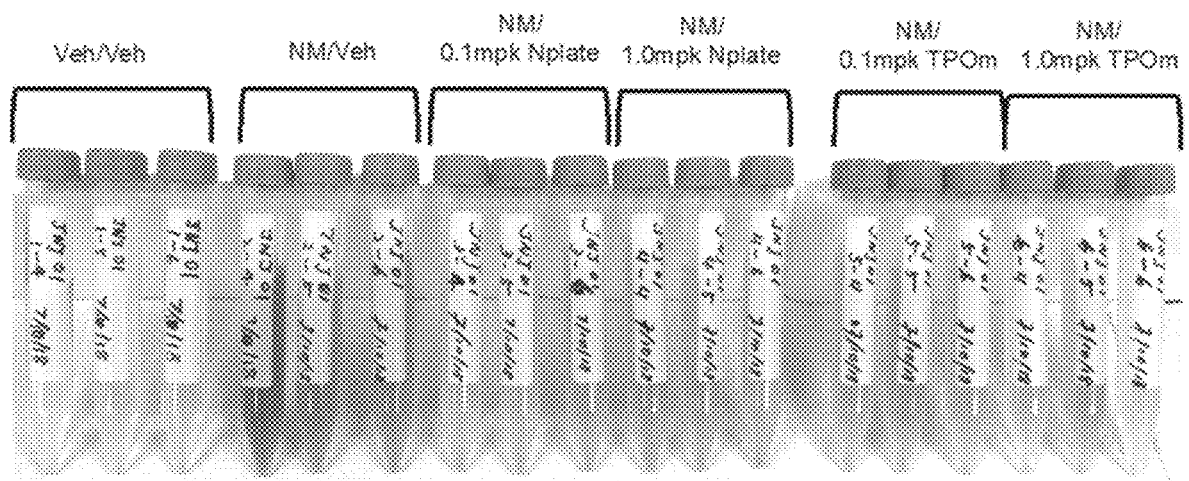
FIGS. 2A-2C show the vascular protective effects of romiplostim treatment observed in the cellular components of the Broncho-Alveolar Lavage (BAL) in a side-by-side comparison with TPOm. In the study, groups of male Wistar rats received the nitrogen mustard (NM). Six hours later, the rats were treated with vehicle, romiplostim or TPOm. On day 4, the relative levels of red blood cells in the BAL were visualized in digital images of the BAL (FIG. 2A) and quantified by measuring the absorbance of the samples at 540 nm (FIG. 2B), while white blood cell (WBC) numbers were determined by hemocytometer counting (FIG. 2C).
Figure 2B:
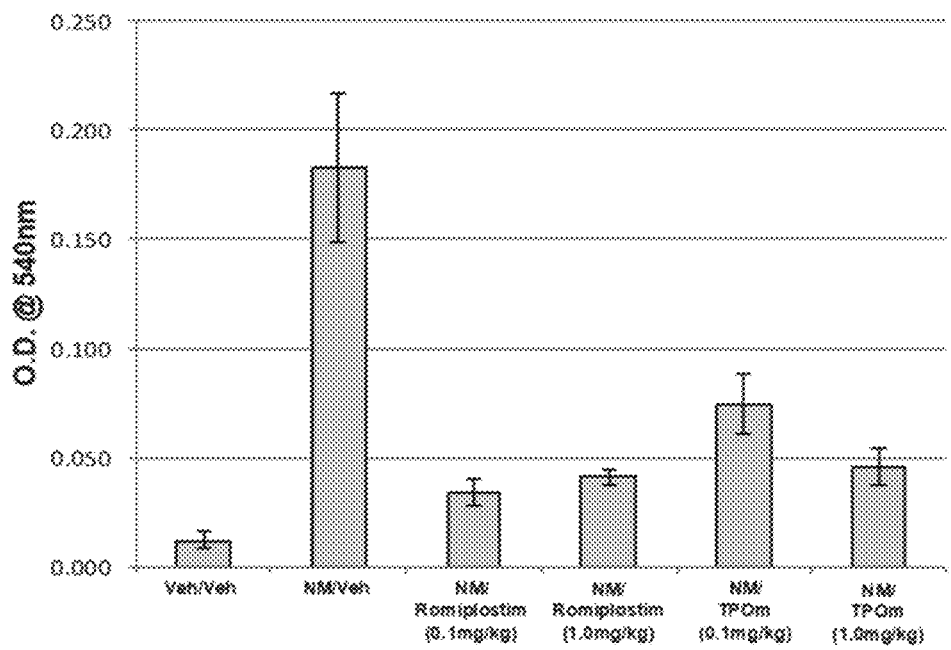
Figure 2C:
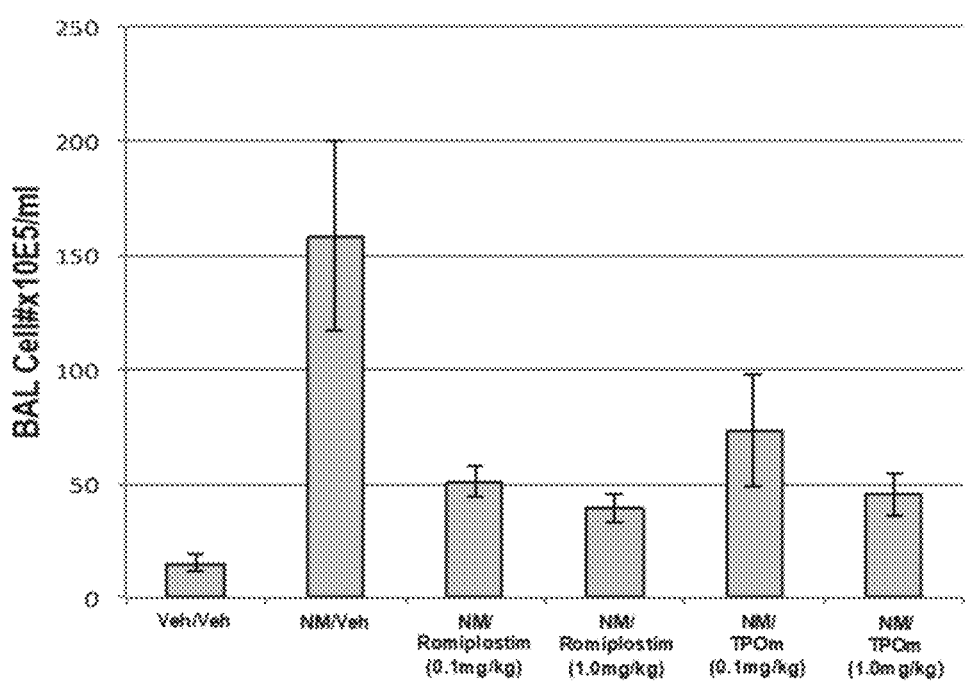

The vascular protective effects of romiplostim treatment (0.1 & 1.0 mg/kg, 6 h post NM-instillation) were observed in the cellular components of the BAL in a side-by-side comparison with TPOm. As shown by assessment of RBC content (FIG. 2A—visual inspection and 2B—optical density) and the WBC content of the BAL (FIG. 2C) indicate that both romiplostim and TPOm administration decreases the micro-hemorrhage and WBC influx into the airspace of the lung induced by NM exposure.

Figure 3A:
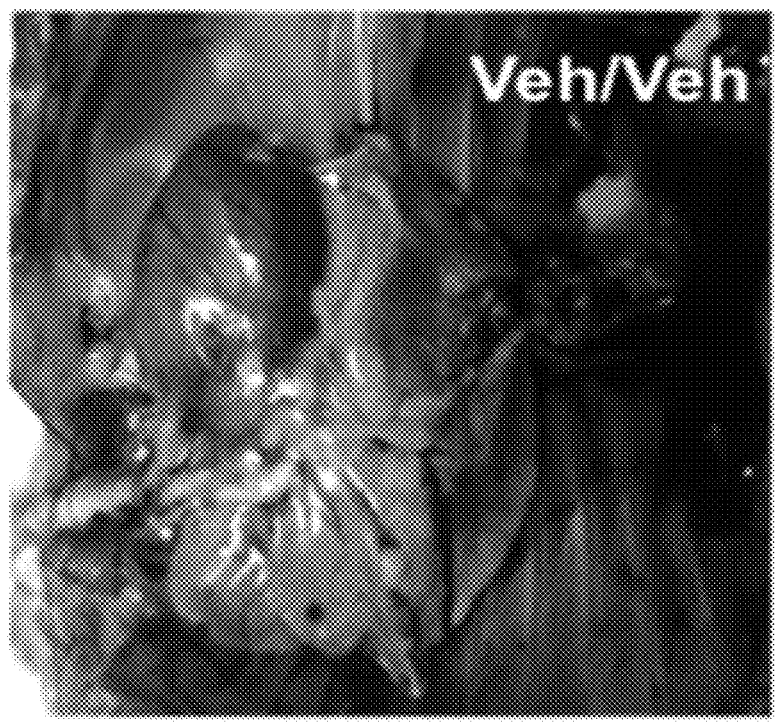
FIGS. 3A-3C show vascular protective effects of TPOm observed in gross organ pathology at necropsy. After the rats were euthanized in the aforementioned studies, the thoracic cavities were surgically opened, and the descending blood vessels were severed. The blood fluids exterior to the collapsed lungs were gently rinsed with Phosphate Buffered Saline (PBS) and blotted with a damp surgical pad. Without perfusing the lung vasculature with PBS, the lungs were digitally photographed.
Figure 3B:
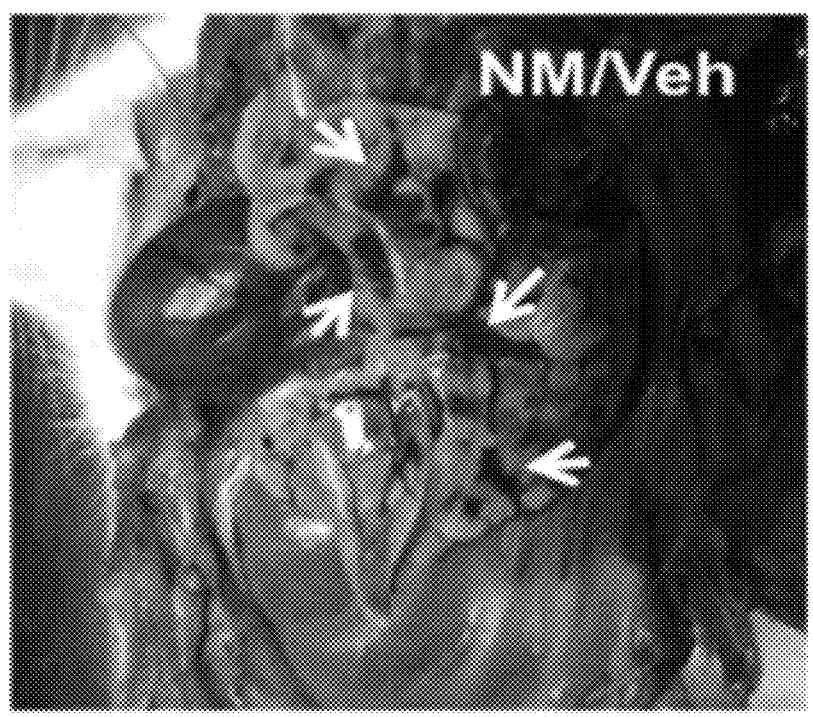
Figure 3C:
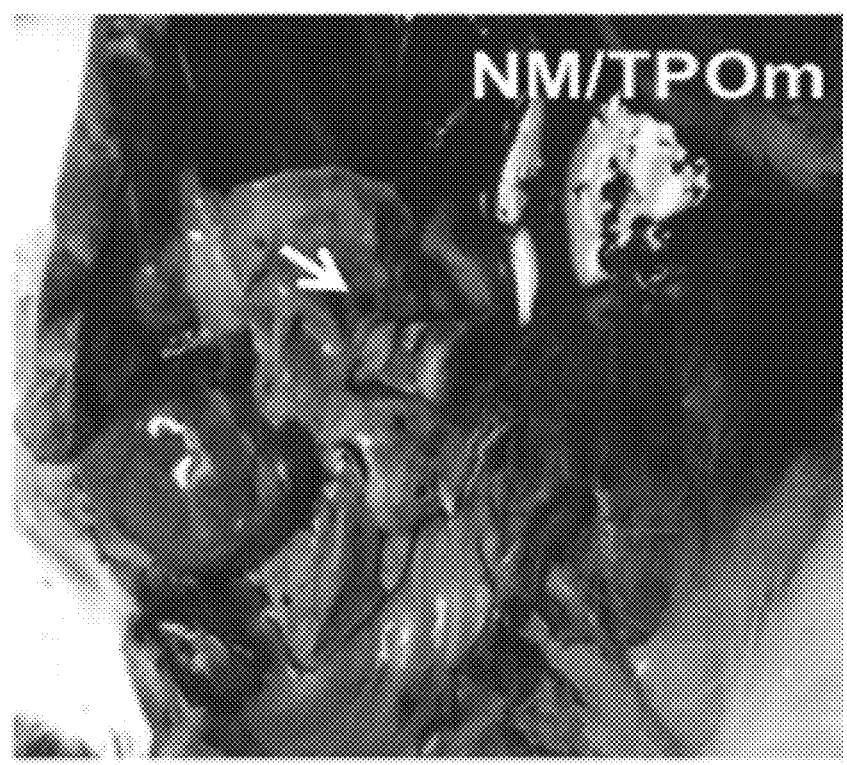
Figure 4:
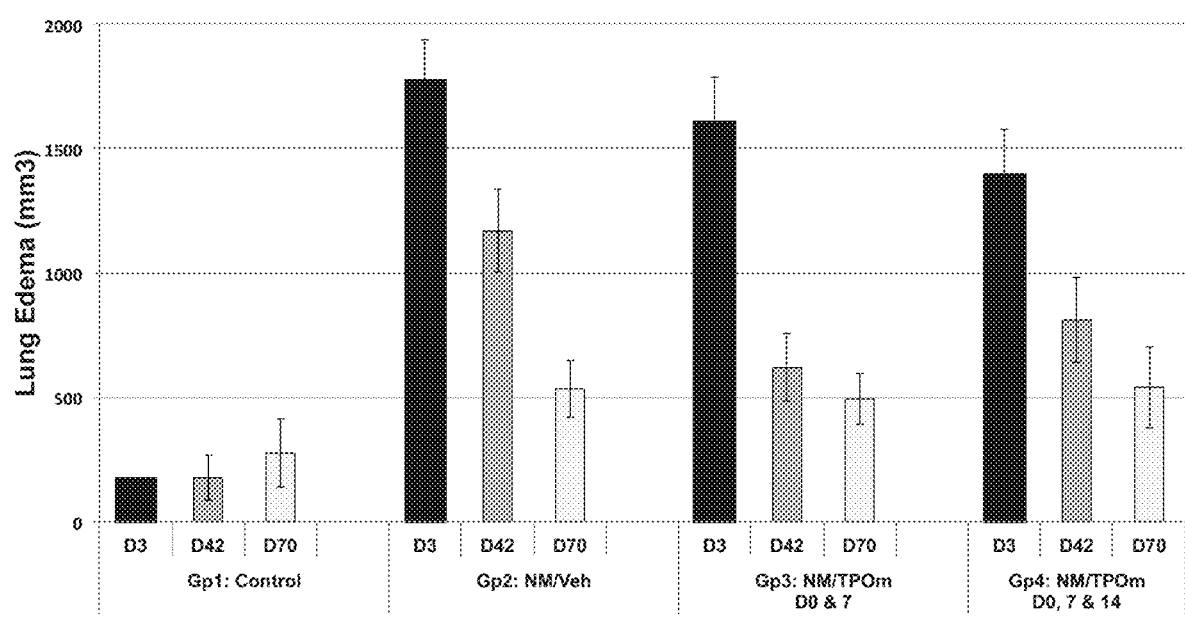
FIG. 4 shows the effects of TPOm on NM-induced pulmonary edema on Days 3, 42, and 70 that develops and recovers after NM exposure as measured by MR imaging using T2-weighted sequences. On Day 3, with a single dose of TPOm administered 6 hours after NM-exposure, the mean edema volume is reduced from 1736 $mm^3$ for the NM-treated group to 1592 and 1387 $mm^3$ for the NM/TPOm-treated groups but this effect is not statistically significant. At later time points, with a second dose of TPOm at Day 7 or Day 7 and 14, mean pulmonary edema volumes were lower in rats treated with TPOm following NM exposure at day 42 and day 70 compared to the test group exposed to NM alone (p=0.0104 for the 6 hour and Day 7 and p=0.0770 for the 6 hour, 7-day and 14-day TPOm groups), suggesting that TPOm accelerates the resolution of the edema.

The vascular protective effects of TPOm were also observed in gross organ pathology at necropsy. As shown in FIGS. 3A-3C, lungs from rats in the vehicle control group exhibit a uniform coloration reflecting blood contained in the pulmonary vasculature at necropsy, while the lungs of rats exposed to NM exhibit numerous sites of sub-plural micro-hemorrhage (arrows) surrounded by pale areas of reduced perfusion. Although NM-exposed rats receiving TPOm exhibit a mottled appearance, the severity and number of micro-hemorrhage sites were markedly reduced compared to rats treated with NM alone. These results indicate that TPOm prevents severe vascular damage associated with the development of micro-hemorrhage and cellular influx following NM exposure.

Effects of TPOm on Pulmonary Edema Following NM Exposure.

The effects of TPOm on pulmonary edema were evaluated following a single dose of TPOm (0.3 mg/kg) at 6 hours on Day 3 and with doses of TPOm at 6 hours and on Day 7 or at 6 hours, on Day 7 and on Day 14 post-NM exposure. On Day 3, with a single dose of TPOm administered 6 hours after NM-exposure, the mean edema volume was reduced from 1736 mm3 for the NM-treated group to 1592 and 1387 mm3 for the NM/TPOm-treated groups but this effect is not statistically significant. At later time points, with a second dose of TPOm at Day 7 or Day 7 and 14, mean pulmonary edema volumes were lower in rats treated with TPOm following NM exposure at day 42 and day 70 compared to the test group exposed to NM alone (p=0.0104 for the 6 hour and Day 7 and p=0.0770 for the 6 hour, 7-day and 14-day TPOm groups), suggesting that TPOm accelerates the resolution of the edema.

Example 2: Effect of TPOm on NM-Induced Pulmonary Fibrosis at Days 42 and/or 70

Materials and Methods

Animals. Male Wistar rats (300-320 grams) were divided into 2 groups: NM/Veh, and NM/TPOm.

Nitrogen Mustard Exposure: In this study, groups of male Wistar rats received 0.125 mg/kg of the sulfur mustard surrogate, mechlorethamine, via tracheal instillation on day 0.

TPOm synthesis and treatments: TPOm was synthesized by Janssen Pharmaceuticals as described previously (see, e.g., U.S. Pat. No. 7,576,056). TPOm was reconstituted in sterile saline, sterile filtered, aliquoted, and stored at −20 C until use. In this extended study examining the effect of TPOm on the development of lung fibrosis out to Day 70, rats received multiple doses of TPOm (0.3 mg/kg) administered at two different dose-timing schedules (6 h, 6 h & day 7 vs. 6 h, day 7 & day 14) following treatment with the NM vesicant.

Magnetic resonance imaging (MRI) measurements: MRI was conducted periodically throughout an extended postexposure period to evaluate levels of pulmonary edema. At 70-day post exposure, the lungs of rats were inflation-fixed in situ to maintain natural pulmonary volumes. The lungs were then excised, fixed overnight in formalin and processed for ex vivo microCT imaging by equilibration with phosphotungstic acid (PTA), a microCT radiographic contrast agent that exhibits a high binding affinity for collagen. This PTA processing method enables the quantitation and visualization of the fibrosis developing in the lung in 2- and 3-dimensions. Each lung was assigned a fibrosis score based on PTA-contrasted 3D microCT images of the lung using a multi-parameter scoring system based on the number and distribution of fibrotic, radiodense foci, appearing in 3-dimentional CT images of lungs processed, ex vivo, with the collagen-specific contrast agent, phosphotungstic acid (PTA). Here, radiodense fibrotic tissue is observed throughout the normal lung parenchyma (light-grey) showing the amount and distribution of pulmonary fibrosis.

TPOm Protects Against NM-Induced Pulmonary Fibrosis in Long Term

The results of this study show that TPOm affects endpoints of NM-induced pulmonary fibrosis. The application of a multi-parameter scoring system developed for the evaluation of pulmonary fibrosis showed that TPOm significantly decreased numerous elements of the fibrotic condition in NM-exposed lung (FIG. 5A). Furthermore, CT images reflecting the radiodensity of PTA-treated lungs showed that TPOm reduced the number and altered the distribution of collagen-containing fibrotic lesions in the lungs of NM-exposed rats (FIG. 5B).

Example 3: Effect of TPOm on NM-Induced Mortality

Materials and Methods

Animals. Male Wistar rats (300-320 grams) were divided into 2 groups: NM/Veh, and NM/TPOm.

Nitrogen Mustard Exposure: A series of preliminary studies was conducted to determine the dose range of NM resulting in the mortality of Wistar rats within a 2-week period. And the results of these studies showed an exceedingly steep NM dose response for animal death with the LD50-LD70 projected between 1.23 & 3.75 mg/kg. Based on the severity of systemic observations in these range-finding studies, the dose of 1.7 mg/kg NM was selected for subsequent studies examining the effect of TPOm on NM-induced mortality. In this study, groups of male Wistar rats (10/group) were treated with a dose of NM projected to be the LD50, 1.7 mg/kg of the sulfur mustard surrogate, mechlorethamine, via tracheal instillation on day 0. Animals were then returned to normal shoebox housing, weighed daily and observed frequently throughout the study period.

TPOm Synthesis and Treatments: TPOm was synthesized by Janssen Pharmaceuticals as described previously (see, e.g., U.S. Pat. No. 7,576,056). TPOm was reconstituted in sterile saline, sterile filtered, aliquoted, and stored at −20 C until use. TPOm was administered as a single dose via sub-cutaneous injection (0.3 mg/kg) 6 hours after exposure to nitrogen mustard (NM).

Figure 6:
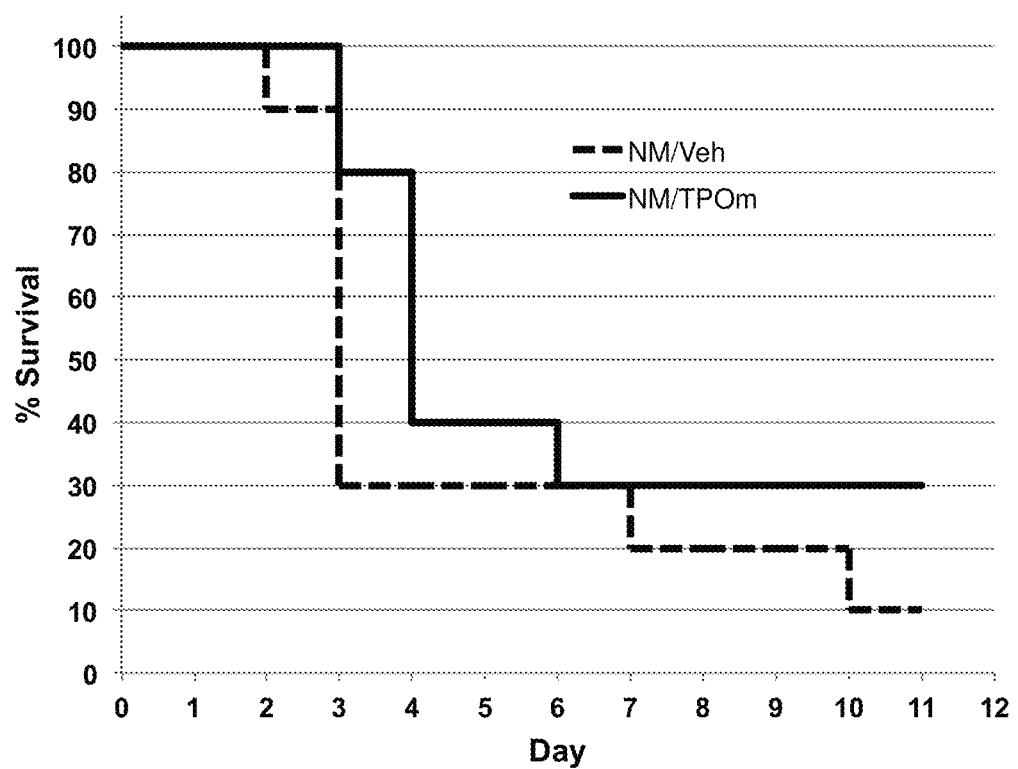
FIG. 6 shows effect of NM-induced mortality. Groups of rats were treated with a dose of NM projected to be the LD50. Animals were returned to normal shoebox housing, weighed daily and observed frequently throughout the study period.

Mortality and bodyweights measurement: Dead animals were tallied while moribund rats were euthanized and tallied as dead and the data were used to construct survival plots (FIG. 6). Daily body weights were also affected with a difference in body weight loss of 5% to 7% (~20 grams) between the NM/Veh and NM/TPOm treatment groups.

Results

TPOm Protects Against NM-Induced Mortality

Results are presented in the plots as shown in FIG. 6. It is apparent from the survival curve (FIG. 6) that the projected LD50 for NM desired for this study was exceeded. This was likely due to the steepness of the dose response and thus the variability in the determination of the LD50. Although the study was not powered sufficiently to resolve significance, it must be noted that TPOm administration 6 h following NM exposure was found to prolong life and resulted in fewer deaths. In addition, body weight reduction was greater for the NM/Veh compared to the NM/TPOm treatment groups with a marked (5% to 7%, ~20 gram) weight loss protection associated with TPOm treatment. The results suggest that TPOm mitigates vesicant-induced mortality and reduces morbidity by protecting against exposure-induced weight loss.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. A method of mitigating a toxic effect of at least one of a vesicant and a caustic gas in a subject in need thereof, the method comprising administering to the subject an effective amount of a thrombopoietin (TPO) mimetic comprising the amino acid sequence of SEQ ID NO:1,
wherein the toxic effect induced by the at least one of the vesicant and the caustic gas is selected from the group consisting of pulmonary vascular damage, pulmonary hemorrhage, pulmonary fibrosis, pulmonary cellular influx, and mortality,
and wherein the vesicant is selected from the group consisting of distilled mustard, mustard gas, lewisite, mustard/lewisite, mustard/T, nitrogen mustard, sesqui mustard, sulfur mustard, phosgene oxime, cantharidin, and furanocoumarin.

2. The method of claim 1, wherein the TPO mimetic is RWJ-800088.

3. The method of claim 1, wherein the TPO mimetic is romiplostim.

4. The method of claim 1, wherein the toxic effect is induced by at least the caustic gas and the caustic gas is selected from the group consisting of hydrogen sulfide, hydrogen fluoride, hydrogen chloride, hydrogen bromide, hydrogen cyanide, arsine, phosphine, nitric oxide, nitrogen dioxide, sulfur dioxide, ozone, chlorine, methylamine, and ammonia.

5. The method of claim 1, wherein the toxic effect is induced by at least the vesicant and the vesicant is nitrogen mustard.

6. The method of claim 1, wherein the effective amount of TPO mimetic is administered to the subject before the subject is exposed to the at least one of the vesicant and the caustic gas.

7. The method of claim 1, wherein the TPO mimetic is administered to the subject while the subject is exposed to the at least one of the vesicant and the caustic gas.

8. The method of claim 1, wherein the TPO mimetic is administered to the subject after the subject is exposed to the at least one of the vesicant and the caustic gas.

9. The method of claim 1, wherein the toxic effect is a pulmonary vascular damage induced by the at least one of the vesicant and the caustic gas.

10. The method of claim 1, wherein the toxic effect is pulmonary hemorrhage induced by the at least one of the vesicant and the caustic gas.

11. The method of claim 1, wherein the toxic effect is pulmonary fibrosis induced by the at least one of the vesicant and the caustic gas.

12. The method of claim 1, wherein the toxic effect is mortality induced by the at least one of the vesicant and the caustic gas.

13. The method of claim 1, wherein the effective amount of the TPO mimetic is administered to the subject by intravenous, intramuscular, intracutaneous, or subcutaneous injection.

14. The method of claim 10, wherein pulmonary hemorrhage induced by the at least one of the vesicant and the caustic gas is a pulmonary microhemorrhage.

15. The method of claim 1, wherein the toxic effect is pulmonary cellular influx induced by the at least one of the vesicant and the caustic gas.

16. A method of mitigating a toxic effect of nitrogen mustard in a subject in need thereof, the method comprising administering to the subject an effective amount of a thrombopoietin (TPO) mimetic comprising the amino acid sequence of SEQ ID NO:1,
wherein the toxic effect induced by the nitrogen mustard is selected from the group consisting of pulmonary vascular damage, pulmonary hemorrhage, pulmonary fibrosis, and pulmonary cellular influx.

17. The method of claim 16, wherein the TPO mimetic is RWJ-800088.

18. The method of claim 16, wherein the TPO mimetic is romiplostim.

* * * * *

SEQUENCE LISTING

```
<160> NUMBER OF SEQ ID NOS: 4

<210> SEQ ID NO 1
<211> LENGTH: 14
<212> TYPE: PRT
<213> ORGANISM: Artificial Sequence
<220> FEATURE:
<223> OTHER INFORMATION: Synthetic Sequence
<220> FEATURE:
<221> NAME/KEY: X
<222> LOCATION: (9)..(9)
<223> OTHER INFORMATION: tryptophan or beta-(2-naphthyl)alanine
<220> FEATURE:
<221> NAME/KEY: X
<222> LOCATION: (14)..(14)
<223> OTHER INFORMATION: alanine or sarcosine
```

<400> SEQUENCE: 1

Ile Glu Gly Pro Thr Leu Arg Gln Xaa Leu Ala Ala Arg Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (9)..(9)
<223> OTHER INFORMATION: beta -(2-naphthyl)alanine
<220> FEATURE:
<221> NAME/KEY: X
<222> LOCATION: (14)..(14)
<223> OTHER INFORMATION: sarcosine

<400> SEQUENCE: 2

Ile Glu Gly Pro Thr Leu Arg Gln Xaa Leu Ala Ala Arg Xaa
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide

<400> SEQUENCE: 3

Ile Glu Gly Pro Thr Leu Arg Gln Trp Leu Ala Ala Arg Ala
1               5                   10

<210> SEQ ID NO 4
<211> LENGTH: 269
<212> TYPE: PRT
<213> ORGANISM: Artificial Sequence
<220> FEATURE:
<223> OTHER INFORMATION: Recombinant peptide

<400> SEQUENCE: 4

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

```
Glu Trp Glu Ser Asn Gly Gln Pro Glu Asn Asn Tyr Lys Thr Thr Pro
            165             170                 175

Pro Val Leu Asp Ser Asp Gly Ser Phe Phe Leu Tyr Ser Lys Leu Thr
            180             185                 190

Val Asp Lys Ser Arg Trp Gln Gln Gly Asn Val Phe Ser Cys Ser Val
        195             200                 205

Met His Glu Ala Leu His Asn His Tyr Thr Gln Lys Ser Leu Ser Leu
        210             215             220

Ser Pro Gly Lys Gly Gly Gly Gly Ile Glu Gly Pro Thr Leu Arg
225             230             235                     240

Gln Trp Leu Ala Ala Arg Ala Gly Gly Gly Gly Gly Gly Gly Gly Ile
            245             250                 255

Glu Gly Pro Thr Leu Arg Gln Trp Leu Ala Ala Arg Ala
            260             265
```